United States Patent [19]

D'Silva

[11] 4,062,969

[45] Dec. 13, 1977

[54] DIOXANE OXIME COMPOUNDS AND PESTICIDAL DIOXANE CARBAMOYLOXIME DERIVATIVES

[75] Inventor: Themistocles D. J. D'Silva, South Charleston, W. Va.

[73] Assignee: Union Carbide Corporation, New York, N.Y.

[21] Appl. No.: 699,960

[22] Filed: June 25, 1976

[51] Int. Cl.$^2$ .............................................. A01N 9/28
[52] U.S. Cl. ................................ 424/278; 260/340.3; 260/340.6

[58] Field of Search ..................... 260/340.6, 340.3; 424/278

[56] References Cited

U.S. PATENT DOCUMENTS 3,153,657   10/1964   Judd et al. ......................... 260/340.3
3,692,835   9/1972   Van Dijk ...................... 260/340.3 X

*Primary Examiner*—Ethel G. Love
*Attorney, Agent, or Firm*—Richard C. Stewart

[57] ABSTRACT

Dioxane oxime compounds are useful as intermediates in the preparation of dioxane carbamoyloxime compounds that exhibit outstanding pesticidal activity.

21 Claims, No Drawings

DIOXANE OXIME COMPOUNDS AND PESTICIDAL DIOXANE CARBAMOYLOXIME DERIVATIVES

This invention relates to 2-oximino-1,4-dioxane and 2-carbamoyloximino-1,4-dioxane compounds and to their preparation. This invention is also directed to insecticidal and miticidal compositions comprising an acceptable carrier and an insecticidally and miticidally effective amount of a carbamoyloxime compound of this invention as well as to a method of controlling insects and mites by subjecting them to an insecticidally or miticidally effective amount of a carbamoyloxime compound of this invention.

More particularly, this invention relates to compounds of the formula:

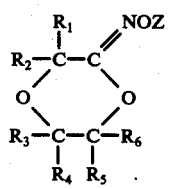

wherein:

$R_1$, $R_2$, $R_3$, $R_4$, $R_5$ and $R_6$ are individually hydrogen or alkyl; or $R_3$, $R_4$, $R_5$ and $R_6$ together may form an alkenylene chain completing a benzene ring which may be optionally substituted with from 0 to 4 substituents selected from among fluoro, chloro, bromo, nitro, cyano, alkyl, alkoxy, alkylthio or trihalomethyl substituents;

Z is hydrogen or

wherein $R_7$ and $R_8$ are individually hydrogen or alkyl; or when $R_7$ is alkyl, $R_8$ may also be alkanoyl or haloalkanoyl;

In general, $R_1$, $R_2$, $R_3$, $R_4$, $R_5$, $R_6$, $R_7$ and $R_8$ substituents individually may not include more than eight aliphatic carbon atoms. Preferred either because of their higher level or pesticidal activity or because of their usefulness as intermediates in the preparation of carbamoyloxime compounds that exhibit outstanding pesticidal activity are the compounds of this invention in which:

$R_1$, $R_2$, $R_3$, $R_4$, $R_5$ and $R_6$ are individually hydrogen or alkyl having from 1 to 4 aliphatic carbon atoms; or $R_3$, $R_4$, $R_5$ and $R_6$ together may form an alkenylene chain completing a benzene ring;

Z is hydrogen or

wherein:

$R_7$ and $R_8$ are individually hydrogen or alkyl having from 1 to 4 carbons. Particularly preferred compounds of this invention are those in which $R_7$ is methyl and $R_8$ is hydrogen.

The carbamoyloxime compounds of this invention are those of the above formula in which Z is

and $R_1$, $R_2$, $R_3$, $R_4$, $R_5$, $R_6$, $R_7$ and $R_8$ are as described above. These compounds exhibit outstanding miticidal and insecticidal activity and may be used as miticides and insecticides utilizing those methods known to those skilled in the pesticidal art. They are also relatively non-toxic to plants and mammals when used in amounts sufficient to kill insects and mites.

The oxime compounds of this invention are those of the above formula in which Z is hydrogen and $R_1$, $R_2$, $R_3$, $R_4$, $R_5$ and $R_6$ are as described above. These compounds are useful intermediates in the preparation of pesticidally active carbamoyloxime compounds. An oxime compound of this invention can be reacted with an appropriately substituted isocyanate compound in the presence of a suitable catalyst to produce the corresponding presticidally active carbamoyloxime compound. For example, 3,3-dimethyl-2-oximino-1,4-dioxane can be reacted with methyl isocyanate in the presence of a trace amount of triethylamine as catalyst to produce 3,3-dimethyl-2-[0-(methylcarbamoyl)oximino]-1,4-dioxane, the corresponding miticidally and insecticidally active carbamoyloxime compound. The oxime compounds of this invention can also be reacted with other chemical species containing electron deficient reaction sites, such as carbamoyl halide compounds or phosgene followed by reaction with an appropriately substituted amine, to produce insecticidally and miticidally active carbamoyloxime compounds.

The compounds of this invention can be prepared in accordance with a variety of methods. One preferred method for preparing the oxime compounds of this invention is illustrated by the general reaction scheme set forth below:

METHOD I

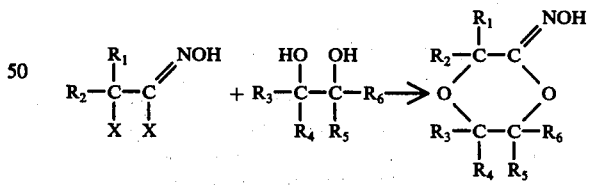

wherein $R_1$, $R_2$, $R_3$, $R_4$, $R_5$ and $R_6$ are as described above and X is halogen, preferably chlorine.

The carbamoyloxime compounds of this invention can be prepared according to a variety of methods which utilize the oxime compounds of this invention as precursors. Three preferred methods are illustrated by the reaction schemes set forth below in which $R_1$, $R_2$, $R_3$, $R_4$, $R_5$, $R_6$, $R_7$ and $R_8$ are described above and X is fluorine or chlorine, except as noted:

METHOD II

-continued

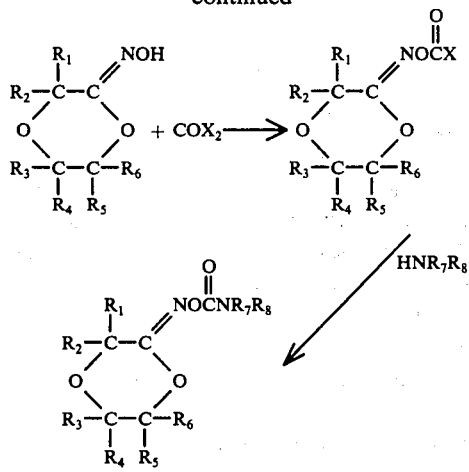

In Method II $R_7$ and $R_8$ are individually hydrogen or alkyl.

METHOD III

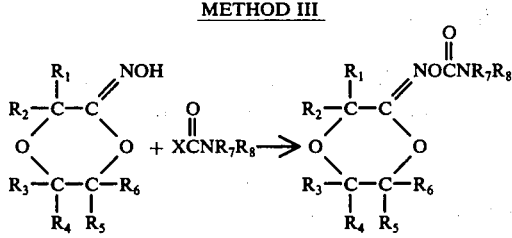

METHOD IV

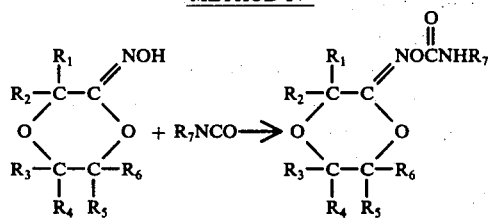

The reactions illustrated in Methods I, II, III and IV are usually carried out by bringing together substantially equimolar amounts of the reactants in an inert solvent. In general, any inert solvent may be used in these reactions. Illustrative of inert solvents which are useful in the conduct of these reactions are benzene, toluene, methylene chloride, xylene dioxane, tetrahydrofuran or the like.

Reaction temperatures are not critical and can be varied over a wide range depending to a large extent on the reactivity and the stability of the reactants. Preferred reaction temperatures are from about $-30°$ C to about $100°$ C.

Reaction pressures are not critical. For convenience the reaction is usually conducted at atmospheric or autogeneous pressure.

These reactions can be conducted in either a homogeneous phase system or a heterogeneous phase system. In the latter as phase transfer agents such as crown ether compounds, quaternary ammonium halide compounds or the like, may be used to facilitate the transfer of the reactants across the phase interface.

The reaction illustrated in Method I is conducted in the presence of a base. The base employed may be either an inorganic or an organic base. Illustrative of organic bases that are useful in the conduct of this reaction are alkali metal alkoxides, alkali metal alkylides or the like. Bases such as alkali metal hydroxides, alkali metal bicarbonates, alkaline earth metal carbonates, alkaline earth metal hydroxides or the like are illustrative of inorganic bases that can be employed in this reaction. Preferred bases are strong inorganic bases such as sodium hydroxide or potassium hydroxide and strong organic bases such as sodium methoxide or sodium glycolate.

The reactions illustrated in Methods II and III are conducted in the presence of an acid acceptor. The molar ratio of the acid acceptor to either reactant is substantially equimolar or a slight excess of the acid acceptor may be used if desired. The acid acceptor used may be either an organic or an inorganic base. Illustrative of organic bases which are useful as acid acceptors in these reactions are tertiary amines, alkali metal alkoxides or the like. Bases such as sodium hydroxide, potassium hydroxide or the like are illustrative of inorganic bases which are useful in the conduit of these reactions. Preferred acid acceptors are tertiary amines such as triethylamine, pyridine, trimethylamine, 1,4-diazobicyclo[2.2.2]octane or the like.

The reaction illustrated in Method IV is preferably conducted in the presence of a catalytically effective amount of a catalyst. In general, any conventional catalyst of the type commonly employed to promote reactions between isocyanate compounds and compounds that contain an active hydrogen can be used. Illustrative of materials that may be used as a catalyst in the conduct of this reaction are organic bases such as organic amines, dibutyltin diacetate or other organo metallic compounds.

The carbamoyloxime compounds of this invention in which $R_8$ is either alkanoyl or haloalkanoyl can be prepared by reacting the corresponding carbamoyloxime compound in which $R_8$ is hydrogen with an appropriately substituted alkanoyl halide compound or anhydride compound.

Carbamoyl halide precursors can be prepared by reacting an appropriately substituted amine with a carbonyl halide such as phosgene in the presence of an acid acceptor.

2-Haloalkylhydroxamoyl halide precursors can be prepared according to conventional methods. For example, 2-haloalkylhydroxamoyl chloride precursors can be prepared by sequentially treating the corresponding 2-haloaldoxime compound with hydrogen chloride and chlorine.

Carbonyl halide, amine, isocyanate and glycol precursors are well known compounds that can be either obtained from commercial sources or prepared by methods well known to those skilled in the synthetic art. Oxime precursors are prepared as described herein above in Method I.

The following specific examples are presented to more particularly illustrate this invention:

EXAMPLE I

Preparation of 2-Oximino-3,3-Dimethyl-1,4-Dioxane

To a solution of sodium (13.8 g) in ethylene glycol (300 ml) cooled to 0° C. was added dropwise with stirring and cooling 2-methyl-2-chloropropionohydroxamoyl chloride (27.0 g) over a period of 1 hour. The reaction mixture was then heated at 50° C. for 2 hours and at 90° for 48 hours. On cooling the reaction mixture was poured into a large excess of ice water followed by extraction with ethyl acetate. The organic extract was washed with water, dried and concentrated. Weight of crude 2-oximino-3,3-dimethyl-1,4-dioxane obtained was 16.8 g.

EXAMPLE II

Preparation of 2-Oximino-3,3-Dimethylbenzodioxane

To a solution of catechol (11.0 g) in 100 ml of water containing 13.2 g of dissolved potassium hydroxide cooled to 10° C was added slowly with stirring and cooling 15.6 g of 2-methyl-2-chloro propionohydroxamoyl. After stirring for 0.5 hours, the reaction mixture was extracted with isopropyl ether. The organic extract was dried and concentrated to yield 20.0 g of 2-oximino-3,3-dimethylbenzodioxane.

EXAMPLE III

Preparation of 3,3-Dimethyl-2-[O-(Methylcarbamoyl)Oximino]-1,4-Dioxane

To a solution of 16.8 g of crude 2-oximino-3,3-dimethyl-1,4-dioxane and 2 drops of triethylamine was added 17 ml of methyl isocyanate. The reaction mixture was left at ambient temperature for 16 hours. The reaction mixture was concentrated and filtered to yield 4.0 g of 3,3-dimethyl-2-[O(methylcarbamoyl)oximino]-1,4-dioxane, m.p. 144°-146° C. (m/e 202).

Anal: Calc'd for $C_8H_{14}N_2O_4$: C, 47.51; H, 6.98; N, 13.86. Found: C, 47.28; H, 7.03; N, 13.83.

EXAMPLE IV

Preparation of 3,3-Dimethyl-2-[O-(Methylcarbamoyl)Oximino]-Benzodioxane

To a solution of 17.9 g of 3,3-dimethyl-2-oximinobenzodioxane and 5 drops of triethylamine was added 18.0 ml of methyl isocyanate. The reaction mixture was then left at ambient temperature for 16 hours. The reaction mixture was concentrated and filtered to yield 3,3-dimethyl-2-[O-(methylcarbamoyl)oximino]benzodioxane, m.p. 174°-176° C.

Anal: Calc'd for $C_{12}H_{14}N_2O_4$: C, 57.59; H, 5.64; N, 11.19.

Found: C, 57.45; H, 5.64; N, 11.34.

The following compounds are representative of other compounds that are within the scope of this invention which can be prepared according to this invention by selecting appropriate starting materials:
2-[O-(methylcarbamoyl)oximino]-1,4-dioxane.
3-Butyl-2-[O-(methylcarbamoyl)oximino]-1,4-dioxane.
3,3-Dimethyl-2-[O-(N-methyl-N-chloroacetylcarbamoyl)-oximino]-1,4-dioxane.
3,3-Dimethyl-2-[O-(butylcarbamoyl)oximino]-1,4-dioxane.
3,3-Dimethyl-2-[O-methylcarbamoyl)oximino]-6-methyl-7-chloro-benzodioxane.
3,3-Dimethyl-2-[O-(methylcarbamoyl)oximino]-7-cyanobenzodioxane.
3,3-Dimethyl-2-[O-(merthylcarbamoyl)oximino]-7-trifluoromethyl benzodioxane.
3,5,6-Trimethyl-2-[O-(methylcarbamoyl)oximino]-1,4-dioxane.
3-Butyl-3-ethyl-2-[O-(N-methyl-N-ethylcarbamoyl)oximino]-1,4-dioxane.
2-[O-(N-ethyl-N-butyrylcarbamoyl)oximino]-6,6-dimethyl-1,4-dioxane.
3-Hexyl-2-[O-(hexylcarbamoyl)oximino]-7-methylthiobenzodioxane.
3,3-Dimethyl-2-[O-(methylcarbamoyl)oximino]-7-methoxybenzodioxane.
3-Methyl-3-Propyl-2-[O-(methylcarbamoyl)oximino]-5-methyl-7-nitrobenzodioxane.
2-[O-(Butylcarbamoyl)oximino]-5,6-difluoro benzodioxane.
2-[O-(Butylcarbamoyl)oximino]-5-methyl-6-propyl-1,4-dioxane.

Selected species of the new compounds were evaluated to determine their pesticidal activity against mites and certain insects, including an aphid, a boll weevil, a caterpillar, a beetle and a fly.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of test compound. The test concentrations in parts per million by weight employed in the tests described hereinbelow were obtained by appropriate dilutions of the stock suspension with water. The test procedures were as follows:

BEAN APHID FOLIAGE SPRAY TEST

Adults and nymphal stages of the bean aphid (*Aphis fabae* Scop.) reared on potted dwarf nasturtium plants at 65°-70° F. and 50-70 percent relative humidity, constituted the test insects. For testing purposes, the number of aphids per pot was standardized to 100-150 by trimming plants containing excess aphids.

The test compounds were formulated by diluting the stock suspension with water to give a suspension containing 500 parts of test compound per million parts of final formulation.

The potted plants (one pot per compound tested) infested with 100-150 aphids, were placed on a revolving turntable and sprayed with 100-100 milliliters of test compound formulation by use of a DeVilbiss spray gun set at 40 psig. air pressure. This application, which lasted 25 seconds, was sufficient to wet the plants to run-off. As a control, 110-110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°-70° F. and 50-70 percent, respectively. Aphids which fell onto the paper and were unable to remain standing after being uprighted were considered dead. Aphids remaining on the plants were observed closely for movement and those which were unable to move the length of the body upon stimulation by prodding were considered dead. Percent mortality was recorded for various concentration levels.

SOUTHERN ARMYWORM LEAF SPRAY TEST

Larvae of the southern armyworm (*Prodenia eridania*, (Cram.)), reared on Tendergreen bean plants at a temperature of 80°±5° F. and a relatively humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–100 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for 3 days. Although the larvae could easily consume the whole leaf within 24 hours, no more food was added. Larvae which were unable to move the length of the body, even upon stimulation by prodding, were considered dead. Percent mortality was recorded for various concentration levels.

MEXICAN BEAN BEETLE LEAF SPRAY TEST

Fourth instar larvae of the Mexican bean beetle (*Epilachna varivestis*, Muls.), reared on Tendergreen bean plants at a temperature of 80°±5° F. and 50±5 percent relative humidity, were the test insects.

The test compounds were formulated by diluting the stock suspension containing 500 parts of test compound per million parts of final formulation. Potted Tendergreen bean plants of standard height and age were placed on a revolving turntable and sprayed with 100–100 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F. for 3 days. Although the larvae could easily consume the leaf within 24 to 48 hours, no more food was added. Larvae which were unable to move the length of the body, even upon stimulation, were considered dead.

FLY BAIT TEST

Four to six day old adult house flies (*Musca domestica*, L.), reared according to the specifications of the Chemical Specialities Manufacturing Association (Blue Book, McNair-Dorland Co., N.Y. 1954; pages 243–244, 261) under controlled conditions of 80°±5° F. and 50±5 percent relative humidity, were the test insects. The flies were immobilized by anesthetizing with carbon dioxide and 25 immobilized individuals, males and females, were transferred to a cage consisting of a standard food strainer about 5 inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a souffle cup containing a one-inch square of an absorbent cotton pad. This bait cup was introduced and centered on the blotting paper under the food strainer prior to admitting the anesthetized flies. The caged flies were allowed to feed on the bait for 24 hours, at a temperature, of 80°±5° F. and the relative humidity of 50±5 percent. Flies which showed no sign of movement on prodding were considered dead.

MITE FOLIAGE SPRAY TEST

Adults and numphal stages of the two-spotted mite (*Tetranychus urticae* Koch), reared on Tendergreen bean plants at 80±5 percent relative humidity, were the test organisms. Infested leaves from a stock culture were placed on the primary leaves of two bean plants 6 to 8 inches in height, growing in a 2½ clay pot. 150–200 Mites, a sufficient number for testing, transferred from the excised leaves to the fresh plants in a period of 24 hours. Following the 24 hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100–100 milliliters of test compound formulation by use of a DeVilbiss spray gun set at 40 psig. air pressure. This application, which lasted 25 seconds, was sufficient to wet the plants to run-off. As a control, 100–110 milliliters of a water solution containing acetone and emulsifier in the same concentrations as the test compound formulation, but containing no test compound, were also sprayed on infested plants. The sprayed plants were held at 80±5 percent relative humidity for 6 days, after which a mortality count of motile forms was made. Microscopic examination for motile forms was made on the leaves of the test plants. Any individual which was capable of locomotion upon prodding was considered living.

The results of these tests are set forth in Table I below. In these tests the pesticidal activity of the compounds against aphid, mite, Southern Armyworm, Mexican Bean Beetle, and house fly was rated as follows:

A = Excellent control
B = Partial control
C = No control

The results of all of these tests are set forth in Table I below:

TABLE I

| Structure | BIOLOGICAL ACTIVITY | | | | |
| --- | --- | --- | --- | --- | --- |
| | Aphid | Mite | Southern Army-worm | Mexican Bean Beetle | Housefly |
| (structure 1) | A | A | A | A | A |
| (structure 2) | A | C | C | A | B |

It will be understood that the insect species employed in the above tests are merely representative of a wide variety of pest that can be controlled by the use of the compounds of this invention. The compounds contemplated in this invention may be applied as insecticides, miticides and nematocides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, amphoteric or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein prevent attack by insects and mites upon plants or other material to which the pesticides are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultraviolet light, oxidation, or hydrolysis in the presence of moisture or, at least such decomposition, oxidation, and hydrolysis as would materially decrease the desirable pesticidal characteristic of the toxicants or impart undesirable characteristics, for instance, phytotoxicity, to the toxicants. The toxicants are so chemically inert that they are compatible with substantially any other constituents of the spray schedule, and they may be used in the soil, upon the seeds, or the roots of plants without injuring either the seeds or roots of plants. They may also be used in combination with other pesticidally active compounds.

What is claimed is:

1. A compound of the formula

wherein:
$R_1$, $R_2$, $R_3$, $R_4$, $R_5$ and $R_6$ are individually hydrogen or alkyl;
Z is hydrogen or

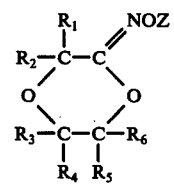

wherein:

$R_7$ and $R_8$ are individually hydrogen or alkyl; and when $R_7$ is alkyl, $R_8$ may also be alkanoyl or haloalkanoyl;

with the proviso that $R_1$, $R_2$, $R_3$, $R_4$, $R_5$, $R_6$, $R_7$ and $R_8$ individually may not include more the eight aliphatic carbon atoms.

2. A compound according to claim 1, wherein Z is hydrogen.

3. A compound according to claim 1, wherein Z is

4. A compound according to claim 1 wherein $R_7$ and $R_8$ are individually hydrogen or alkyl having from one to four carbon atoms.

5. A compound according to claim 1 wherein $R_7$ is alkyl and $R_8$ is hydrogen.

6. A compound according to claim 1 wherein $R_7$ is methyl or ethyl and $R_8$ is hydrogen.

7. A compound according to claim 1 wherein $R_1$, $R_2$, $R_3$, $R_4$, $R_5$ and $R_6$ are individually hydrogen or alkyl having from 1 to 4 carbon atoms.

8. 2-Oximino-3,3-dimethyl-1,4-dioxane.

9. 3,3-Dimethyl-2-[0-(methylcarbamoyl)oximino]-1,4-dioxane.

10. An insecticidal and miticidal composition comprising an acceptable carrier and as the active toxicant an insecticidally or miticidally effective amount of a compound of the formula

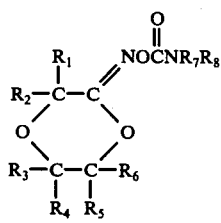

wherein:

$R_1$, $R_2$, $R_3$, $R_4$, $R_5$ and $R_6$ are individually hydrogen or alkyl;

$R_7$ and $R_8$ are individually hydrogen or alkyl; and when $R_7$ is alkyl, $R_8$ may also be alkanoyl or haloalkanoyl;

with the proviso that $R_1$, $R_2$, $R_3$, $R_4$, $R_5$, $R_6$, $R_7$ and $R_8$ individually may not include more than eight aliphatic carbon atoms.

11. A composition according to claim 10 wherein $R_7$ and $R_8$ are individually hydrogen or alkyl having from 1 to 4 carbon atoms.

12. A composition according to claim 10 wherein $R_7$ is alkyl and $R_8$ is hydrogen.

13. A composition according to claim 10 wherein $R_7$ is methyl or ethyl and $R_8$ is hydrogen.

14. A composition according to claim 10 wherein $R_1$, $R_2$, $R_3$, $R_4$, $R_5$ and $R_6$ are individually hydrogen or alkyl having from 1 to 4 carbon atoms.

15. A composition according to claim 10 wherein said active toxicant is 3,3-dimethyl-2-[0-(methylcarbamoyl)oximino]-1,4-dioxane.

16. A method of controlling insects and mites which comprises subjecting them to an insecticidally or miticidally effective amount of a compound of the formula:

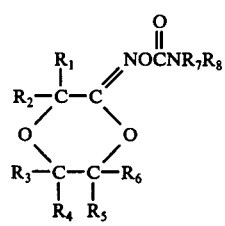

wherein:

$R_1$, $R_2$, $R_3$, $R_4$, $R_5$ and $R_6$ are individually hydrogen or alkyl;

$R_7$ and $R_8$ are individually hydrogen or alkyl; and when $R_7$ is alkyl, $R_8$ may also be alkanoyl or haloalkanoyl;

with the proviso that $R_1$, $R_2$, $R_3$, $R_4$, $R_5$, $R_6$, and $R_7$ and $R_8$ individually may not include more than eight aliphatic carbon atoms.

17. A method according to claim 16 wherein $R_7$ and $R_8$ are individually hydrogen or alkyl having from 1 to 4 carbon atoms.

18. A method according to claim 16 wherein $R_7$ is alkyl and $R_8$ is hydrogen.

19. A method according to claim 16 wherein $R_7$ is methyl or ethyl and $R_8$ is hydrogen.

20. A method according to claim 16 wherein $R_1$, $R_2$, $R_3$, $R_4$, $R_5$ and $R_6$ are individually hydrogen or alkyl having from 1 to 4 carbon atoms.

21. A method according to claim 16 wherein said compound is 3,3-dimethyl-2-[0-(methylcarbamoyl)oximino]-1,4-dioxane.

* * * * *

UNITED STATES PATENT OFFICE
CERTIFICATE OF CORRECTION

Patent No. 4,062,969           Dated  December 13, 1977

Inventor(s) Themistocles D.J. D'Silva

It is certified that error appears in the above-identified patent and that said Letters Patent are hereby corrected as shown below:

Column 10, lines 50 to 54 which read, $-\overset{O}{\underset{\|}{\phantom{C}}}-$  should read,  $-\overset{O}{\underset{\|}{C}}NR_7R_8$

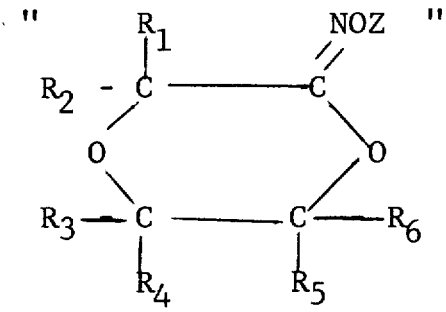

Column 10, lines 60 to 66 which read -- 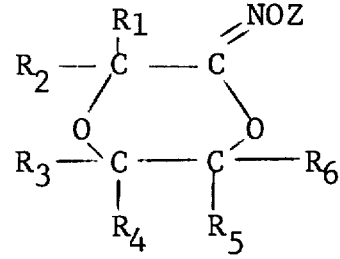

should read " $-\overset{O}{\underset{\|}{C}}NR_7R_8$ ".

Signed and Sealed this

Third Day of October 1978

[SEAL]

Attest:

RUTH C. MASON  
Attesting Officer

DONALD W. BANNER  
Commissioner of Patents and Trademarks